United States Patent [19]

Allen

[11] 4,441,576

[45] Apr. 10, 1984

[54] NONLINEAR PASSIVE ACOUSTIC FILTERING

[76] Inventor: Clayton H. Allen, 651 Concord Ave, Cambridge, Mass. 02138

[21] Appl. No.: 369,850

[22] Filed: Apr. 19, 1982

[51] Int. Cl.³ .............................. H04R 25/02
[52] U.S. Cl. ..................... 181/129; 181/135; 128/152; 179/107 E; 179/156 R; 179/182 R
[58] Field of Search .......... 181/129, 130, 135; 128/152; 179/184, 186, 182 R, 107 R, 107 E, 156 R

[56] References Cited

U.S. PATENT DOCUMENTS 2,529,562  11/1950  Martin ............................ 179/182 R

*Primary Examiner*—Benjamin R. Fuller
*Attorney, Agent, or Firm*—Charles Hieken

[57] ABSTRACT

In an ear muff intended for protection against excessive noise exposure, the passive means according to this invention automatically and continuously varies the amount of reduction provided for the sound arriving at the ear of the wearer; it retains substantially unaltered the performance of the ear muff for high sound levels, but effects a prescribed lesser value of sound reduction at low sound levels and maintains coherent phase relations between the sound waves arriving at the two ears as needed for reception of directional information.

21 Claims, 23 Drawing Figures

NONLINEAR PASSIVE ACOUSTIC FILTERING

This invention relates to the field of hearing protection and more particularly to the improvement of the ear muff type protectors and devices providing passive acoustic filtering between an outside source of sound and the ear.

Ear protection is needed to prevent a loss in hearing acuity and the gradual increase in the threshold of hearing resulting from extended exposures to loud noise as encountered, for example, in many industrial working environments and in some forms of active military service.

Noise exposure is evaluated by measuring both the oscillating pressure amplitude of sound waves incident upon the ears and the length of time a person is exposed to such pressure amplitude.

Because of the wide range of sound pressure amplitudes that the ear can hear, the linear value of sound pressure itself becomes cumbersome to handle and is usually replaced by a logarithmic measure called sound pressure level (abbr. SPL) and is expressed in terms of decibels (dB) defined by the relation $$SPL = 20 \log p/p_o \text{ dB } re \ 2 \times 10^{-5} \ N/m^2$$

where:
SPL is the sound pressure level in dB re $2 \times 10^{-5}$ N/m$^2$
p is the sound pressure amplitude, often called simply the sound pressure, Newtons/meter$^2$ (N/m$^2$)
$p_o$ is the reference pressure which has been standardized as $2 \times 10^{-5}$ N/m$^2$ The terms "Sound reduction" or "Noise reduction" (NR) refer to and designate the dB difference in SPL under two specified conditions. The noise reduction of an ear muff is the difference between the SPL at the ear without any protective device and the SPL at the ear when the ear muff is properly positioned and held against the head, covering the ear.

The term "Attenuation" may have a number of definitions, but as used here, it designates the decibel change in SPL of a sound wave in passing from one point to another along its transmission path.

It is widely accepted that a negligible hazard to hearing results when healthy ears are exposed as much as several times a day to individual impulses of noise that do not exceed peak levels of 140 dB, but ears should be provided with some form of protection giving sufficient NR to reduce impulses with higher peak levels to no more than 140 dB, even when only a few impulses are encountered in a day.

For continuous noise, the relative hazard of "noise induced hearing loss" or "hearing threshold shift" can be evaluated well enough for engineering purposes by use of the single number, A-weighted sound level (expressed in dBA), which is determined by passing the electrical signal from a sound level meter through a standard A-weighting filter before applying the signal to the indicating meter. The A-weighting filter reduces the importance of low frequency sounds relative to the higher frequencies according to a standardized relation.

It is widely agreed that negligible hazard to hearing results when healthy ears are exposed repeatedly for long durations to noise that measures less than 75 dBA. Higher levels can be tolerated without serious hazard if the duration of the daily exposure is limited, but the tradeoff between SPL and duration is a matter of some variation. The Occupational Safety and Health Administration (OSHA), under the United States Department of Labor, responsible for controlling noise exposure in American industry now accepts an averaged A-weighted level of 90 dBA for an 8-hour daily exposure and allows higher averaged A-weighted levels for reduced daily exposure times at an exchange rate of 5 dBA increase in level for each halving of the exposure time up to a level of 115 dBA for a limit of 15 minutes a day. Other enforcement agencies, including the U.S. military forces, use different limits and exchange rates, but the principle of evaluating the noise exposure hazard is similar.

It is not necessary to reduce all noise below a fixed level, but using OSHA regulations (in effect 1982), for example, three conditions must be met:
(1) The total daily exposure comprising the combined effect of A-weighted sound level and time may not exceed 90 dBA.
(2) A-weighted random noise levels may not exceed 115 dBA, even for short periods of time.
(3) Impulse peak levels may not exceed 140 dB (measured with flat weighting, no filter).

The present invention is designed to aid in meeting these requirements and in providing simultaneously, an improved hearing of low level speech and other sound signals important to the safety and comfort of the wearer of sound protective ear muffs.

An ear muff of conventional design provides an amount of NR at the ear that is independent of the SPL incident upon the ear muff. An ear muff designed to provide 30 to 50 dB of NR in the frequency region from 500 to 8000 Hz, as needed to protect the ear against extended exposures to incident SPL in the range from 120 to 140 dB re $2 \times 10^{-5}$ N/m$^2$ will provide the same NR for weaker sounds, such as voice communication and other informative low level acoustic signals, that are important to the job performance and to the safety of the person being protected. For example, government regulations require mobile machinery to sound an audible warning when backing and ear muffs impede perception of the warning.

Low level signals are then less audible, and in some instances inaudible, where the wearer may already have encountered severe hearing loss through previous noise exposure, sickness or trauma. By this means the use of conventional hearing protectors produces a feeling of isolation with its resulting discomfort for the wearer and may contribute to a decrease in job performance and an increase in the potential hazard of physical injury or accident. This situation is accentuated by the fact that conventional ear muffs produce more NR (30 to 50 dB) in the high frequency regions (500 to 8,000 Hz) that conveys most of the definitive speech signals and less NR (10 to 20 dB) in the region below 400 Hz that often carries high levels of noise characteristic of large power sources, such as transformers, motors, and engines. These low frequency signals often are then loud enough at the ear to reduce the intelligibility of speech and other signals by partially masking the more attenuated high frequency components.

Limits of noise exposure set by OSHA for industrial workers generally cannot be met by engineering or administrative noise control methods. A long history of development of devices for controlling noise in the workplace have, in many situations, failed to provide economically viable means to reduce noise to acceptable levels. Although effort continues to reduce noise of existing sources, personal ear protective devices are often needed at this time to reduce the noise levels at the ears to acceptable levels.

All ear muffs of conventional design are hazardous in that they interfere with the ability of the wearer to hear important low level signals or to locate the direction of the sources of such signals and, in that way they contribute to accidental contact with moving vehicles or hazardous machinery and the like. For this reason OSHA has been resistant to the use of personal ear protective devices and has permitted their use only as a last resort, even in instances where the reduction of noise by other means may interfere with production or involve costs that erode competitive position in the marketplace and ultimately increase the cost of goods to the consumer.

Concurrent with this resistance of OSHA, there has been a resistance of workers to the wearing of ear protective devices. Physical discomfort is one factor in such resistance, but that form of discomfort is generally minor inasmuch as it is usually overcome in the same way that discomfort of wearing glasses, face masks or protective clothing is overcome; the more persistent discomfort arises from the feeling of isolation and the loss of the ability to hear clearly speech and other signals important to the safety, performance and welfare of the wearer.

Accordingly, it is an important object of the invention to provide a personal protective device that provides protection against high level noise and simultaneously permits the wearer to hear clearly and locate the direction of low level audible signals.

Historically, it is known that a nonlinear acoustic element, comprising a small orifice in an earplug acts to permit the passage of low level sounds, such as speech, through the earplug with a small amount of noise reduction (NR) while at the same time, providing substantially the full NR capability of the unmodified earplug against high level noise, such as gun blasts or the like.

Such earplugs were developed by this inventor as early as 1961. Their NR characteristics were measured in the laboratory and experimentally evaluated on using personnel. Samples were field tested by the Surgeon General's Office of the U.S. Army and found to function advantageously to prevent excessive noise at the ear when used during rifle fire and to automatically permit clear hearing of verbal commands between firings. These earplugs were not accepted at that time for use in the military application of protecting against gunfire, for which they were designed, because of the possibility that they might be misused in other applications such as for providing protection in noisy vehicles or around aircraft. In the latter applications, sustained, moderately high noise levels, lying generally in the intermediate range between the speech levels and the peak levels of rifle fire, would pass through the earplug with inadequate noise reduction to protect the ear for longterm exposure.

That earplug design was released later (1969) to the British Royal Naval Establishment where tests by the Royal Naval Research Committee verified the earlier results of this inventor and the design was accepted for use by British military personnel. Since then, that amplitude-sensitive earplug design has been manufactured by Amplivox Hearing Conservation Limited, Beresford Ave., Wembly, Middlesex, England, under the trademark "Gunfender".

The problem of adapting such an amplitude sensitive means to operate in the A-weighted sound level region between 90 and 140 dBA, characteristic of the random noise in industrial environments, in military vehicles or around aircraft, remained unsolved for over 20 years.

Accordingly, it is an important object of this invention to provide means for automatically, continuously and passively varying the noise reduction of an ear muff in response to the magnitude of the incident sound pressure.

It is a further object to provide means for effecting a useful variation of noise reduction in the range of incident sound pressures encountered in noisy industrial environments.

It is a further object to provide a low sound attenuation for low incident sound levels and retain a spectral fidelity favorable to the reception and recognition of such sounds in intervals between the occurrence of high level sounds.

It is a further object to provide means for binaural hearing of low level sounds by retaining at the ears, substantially the same phase relations between sound waves arriving at opposite sides of the head as would exist in the absence of any ear protection.

It is a further object to minimize the effect of the ear muff shell vibration, the effect of reverberation within an ear muff, and the effect of small sound leakage around the edge of an ear muff.

It is a further object to retain the maximum sound attenuation of a conventional ear muff when it is modified by the present invention and is exposed to high levels of incident sound.

It is a further object to provide a range of modifying means suitable for application to any of a large number of conventional ear muff designs.

It is a further object to provide means for optimizing the nonlinear noise reduction characteristics of an ear muff intended for use in specified noise environments so as to give adequate ear protection against the high sound levels typical of the specified environment and to give improved reception of the important low level sounds normally anticipated.

It is a further object to provide interchangeability of the modifying means.

It is a further object to provide means for quick visual identification of the environment for which the modifying means is suitable.

It is a further object to provide means for accommodating the cooperative use of an earphone within the ear muff enclosure.

It is a further object to provide means for automatically, continuously and passively varying the NR of a semi-insert type ear protector to improve the reception of speech and other low level acoustic signals while simultaneously preserving or increasing the maximum NR normally expected from such a device for impulses and other high level sounds.

It is a further object to provide means for protecting a microphone against acoustical overload or damage from large acoustic pressures or impulses while allowing low level acoustic signals to reach the microphone with little attenuation and little distortion during intervals of low sound pressure.

It is a further object to provide passive means to limit the acoustical sound pressure amplitudes produced at the ear by a hearing aid.

It is a further object to provide means for automatically, continuously and passively varying the attenuation of sound transmitted through a sound barrier in response to the magnitude of the instantaneous pressure of a sound wave incident upon the barrier.

The present invention provides means for automatically and continuously altering the amount of NR produced by an ear muff in response to the magnitude of the incident SPL.

At high incident SPL an ear muff that is modified according to the present invention will retain substantially the full NR and therefore the full protection capability of the unmodified ear muff.

At low incident SPL an ear muff that is modified according to the present invention will provide a prescribed reduced value of NR and thereby will allow speech and other intelligible sound signals to be heard clearly in the intervals between the occurrence of high, random values of SPL or peak impulse levels that occur at irregular, unpredictable rates in industrial and in military environments.

The problems addressed and solved by the present invention include:

1. Provision of means to attain a low value of NR at low incident SPL when the ear is enclosed by the large volume of the ear muff cavity.
2. Provision of means to equalize or advantageously control the spectral shape of the NR at low incident SPL.
3. Provision of means to reduce the transition level of the incident SPL at which the nonlinear means changes from its low level (constant NR) mode of operation to its high level (increasing NR) mode of operation so that the transition level can be advantageously designed to occur within the range normally encountered in industrial noise environments or the like.
4. Provision of means for preserving at the ears, the major definitive aspects of the phase relations between sound waves that arrive at opposite sides of the head.
5. Provision of means for increasing the rate of change of NR in the high level mode of operation so that the NR will increase faster than the rate of 5 dB increase in NR for 10 dB increase in the incident SPL, that has long been known as characteristic of an orifice operating in the nonlinear range.

Previous experience with the nonlinear earplug revealed that, for a specified design of the nonlinear element (generally a round, sharp edged orifice); there, is a well-defined transition value of the incident SPL below which the element acts as a linear device (producing an NR that is constant independent of the incident SPL) and above which the element becomes a non-linear device (producing an NR that increases at a rate that closely approaches half the rate of increase of the incident SPL). It was found that the transition value of the incident SPL decreased with the size of orifice and sharpness of its edge.

One part of the problem encountered in applying the nonlinear orifice concept to an ear muff is that it requires an increase in open area to accommodate the larger enclosed volume of the ear muff, nearly 100 times the volume of the cavity of the ear canal behind an earplug. To increase the open area and keep the orifice dimensions small, a plurality of small orifices have been used successfully, for example, as many as 76 circular sharp-edged orifices have been produced in a 5-mil brass sheet sealed to a massive surrounding ring that held the sheet stationary.

Experiments with orifices of different sizes and shapes have resulted in the recognition of a number of designs that are suitable for various applications. In particular it has been discovered that a slit formed between the sharp edges of razor blades has a low viscous flow resistance and provides a relatively large air flow with a lower transition SPL than was obtained with a plurality of round, sharp-edged orifices. For example, a 6-mil wide slit reduced the transition SPL to as low as 106 dB for a 200 Hz sound and 126 dB for a 2,000 Hz sound. With much narrower slits, however, a reverse effect occurred, the transition SPL rose again and was above 140 dB for a 1-mil slit for all frequencies, in the range from 500 to 2,000 Hz.

When various nonlinear elements were installed in a conventional ear muff, it was observed that, for any of them, the sound they admitted was effectively short-circuited by the low acoustic impedance of the cavity enclosed by the ear muff. This greatly reduced the SPL at the ear, particularly at high frequencies, making speech reception difficult.

Similar tests made on nonlinear elements operating into an anechoically terminated ½-inch diameter duct instead of an ear muff, showed much more uniform NR over the same frequency range.

At low low sound levels, the NR was independent of incident SPL below 90 dB, but for some orifice configurations, it did still increase approximately 15 dB over the frequency range from 200 to 4,000 Hz because of the mass reactances of the orifice members operating into the resistive impedance of the duct.

At high incident SPL, on the other hand, the NR increases 5 dB for each 10 dB increase in incident SPL because the acoustic impedance of the orifice is then dominated by the acoustic resistance of the orifice which increases due to increased turbulence in the air flow, but that NR is substantially constant across the frequency range, because the resistance due to turbulence in the jet, and the acoustic resistance of the duct are both independent of frequency.

These results led to the use of a tube between the nonlinear orifice and the ear to confine the sound and avoid the short-circuiting effect of the large volume within the ear muff. An experimental model was constructed using a nonlinear element comprising a 2-mil, 3/16 inch long slit between razor blades. This was combined with a conventional ear muff and a short length PVC tubing serving as the duct between the orifice and the simulated ear. A soft resilient flange of 1/16 inch rubber was added to the end of the tube to rest against the pinna of the simulated ear to aid in confining the sound at the ear. The ear muff was pressed against the simulated head around the ear. Sound was directed at the external surface of the orifice and measured there as the incident SPL. Sound was also measured with a microphone that acted as a termination of the simulated ear canal at the eardrum position. For this arrangement the NR is less and the transition SPL is somewhat higher than for the 6-mil slit operating into an anechoically terminated duct. The explanation is, first of all, the slit is narrower, but more important to the understanding of the action of an ear muff is the fact that the microphone at the eardrum position does not act as an anechoic termination, but instead acts more like a real eardrum and reflects some sound back along the duct toward the orifice. The result is:

1. An increase in SPL and a corresponding decrease in NR within the duct due to the added pressure of the reflected wave.
2. A decrease in the air flow velocity through the orifice, because the increased SPL in the duct decreases the pressure difference across the orifice.
3. An increase in the transition SPL because a higher incident SPL is required to regain the air flow speed needed to produce the turbulent resistance responsible for the nonlinear operation.
4. A resonant reinforcement of the SPL at the eardrum and at the orifice in the frequency range covered by the octave band centered at 2,000 Hz; this is due to the longitudinal resonance of the duct between the orifice and the microphone, acting as an eardrum.

The NR was substantially independent of incident SPL below 110 dB but approached an increase of 5 dB for an increase of 10 dB in the incident SPL in the range of 130 to 160 dB as for the 6-mil slit operating in the anechoically terminated tube.

The resonant reinforcement of the SPL at the ear near 2000 Hz was an important result since it demonstrated the ability of altering the NR spectrum and improving the fidelity of presentation of the incident sound to the ear. The resonance illustrated by these data was too sharp and it excessively decreased the NR at 2000 Hz. However, this resonance can be broadened by the addition of a small amount of acoustical absorption in the duct or by adding a side branch resonator to partially counteract the longitudinal resonance of the duct itself. Such techniques are well-known to those experienced in the art.

For some applications it is advantageous to reduce the value of the transition SPL. This result can be achieved by causing turbulence in the air flow to occur at a lower speed. Means for creating turbulence at a lower flow speed include:

(1) Increasing the perimeter of the jet, such as by replacing a round orifice with a long slit.
(2) Sharpening the orifice edge, such as by using razor sharp edges.
(3) Further increasing the perimeter by creating a saw-toothed shape or roughening the slit contour.
(4) Introducing a solid spoiler into the air stream 1 to 5 diameters (or slit-widths) away from the orifice. It is desirable to use such a spoiler on both the entrance and exit for such an orifice, because a sound wave reverses, and it is equally important to act in both directions.

For some applications it is advantageous to increase the rate at which NR rises as the incident SPL increases. To accomplish this, a plurality of orifices may be located one after the other in series. When the orifices are separated sufficiently they act independently of each other and their effects are cumulative.

For example, a 2-mil slit by itself operated at 1000 Hz into an anechoically terminated $\frac{1}{2}$-inch duct produced a transition SPL of 124 dB. At low SPL the NR was 7 dB and at 160 dB the measured NR was 25 dB, an increase of 18 dB. When this slit was followed by a second slit, separated from it by approximately $\frac{1}{8}$ inch, the transition SPL increased to approximately 128 dB, because the added resistance of the second slit decreased the effective pressure drop across the first slit and necessitated an increase in the incident SPL to regain the air flow speed required for the onset of turbulence. The constant NR in the duct for this combination was approximately 22 dB for all values of incident SPL below the transition level. When the incident SPL was increased above the transition level, the NR increased at a rate half as fast as the incident SPL (i.e., 5 dB increase in NR for 10 dB increase in incident SPL) until a second transition level of 148 dB was reached, at which point the NR increased at a rate $\frac{1}{4}$ as fast as the incident SPL (i.e., $2\frac{1}{2}$ dB increase in NR for 10 dB increase in incident SPL).

The second transition occurred when the SPL (generated by the sound entering the cavity between the two orifices) reached a level sufficient to cause the second orifice to become nonlinear; its resistance then increased and created an increase in NR at the rate of 5 dB for each 10 dB of increase in the SPL applied to it, or $2\frac{1}{2}$ dB for each 10 dB of the incident SPL applied to the first slit. Thus, after the second transition the total NR of both slits reached $7\frac{1}{2}$ dB for each 10 dB increase in the incident SPL. At 160 dB the total NR was 42 dB, an increase of 20 dB over the constant NR at low values of incident SPL. The increase in NR at 160 dB over that for low sound levels for this combination is only 2 dB more than for the single 2-mil slit, but it is apparent that the difference will be increasingly greater for higher levels of incident sound, such as might be encountered from artillery fire.

The advantage of the second slit will become greater as the transition level of each slit is lowered. It is of course possible to use large numbers of slits in series, although that may be expected rapidly to reach the point of diminishing return. In principle, at least, the NR can be made to approach the rate of increase of the incident SPL, in which case the SPL at the ear will approach a cut-off limit. This may be important in some applications.

An important advantage of the present invention lies in the function of the duct between the orifice and the ear in cooperation with a soft resilient flange that rests with a light pressure against the pinna of the ear. This assembly serves to reduce or eliminate the effects of sound radiation from vibrating interior surfaces of hard shell, the effects of small amounts of sound leakage under the ear muff cushion and the effects of reverberation within the ear muff cavity, by partially restricting the entrance or reentrance of such sounds into the region near the ear that is covered by the soft flange. By substantially reducing these uncontrolled sounds, the sound admitted through the orifice assembly, particularly at low sound levels, arrives at the ear substantially as a progressive wave that carries the essential phase relations of the incident sound signal.

Thus, the phase relations between the waves striking opposite sides of the head are preserved at the ears and binaural source location, essential to the safety and well-being of the person, becomes simply a matter of course.

Such source location is generally found to be impossible with unmodified ear muffs of conventional designs. The person feels isolated and often disoriented, unable to determine which way to move in an emergency, even when a hazard is audible, but not clearly in view.

An ear muff modified according to the teaching of this invention retains for the wearer a sense of presence and orientation as well as an ability to communicate and to hear clearly low level signals that occur in the intervals between high level peaks or impulses. By this means the modified ear muff encourages its own proper use by eliminating the sense of need to lift the ear muff or wear it with a leak under the cushion in order to feel "safe." The wearer will find greatest comfort and security when the ear muff is properly worn.

The nonlinear means for controlling noise reduction of an ear muff, as described herein, can be used to supplement the performance of an intercom system when earphones are installed in ear muffs or in specially designed circumaural ear enclosures that are normally used to exclude external noise. When such an earphone assembly is used in an application where audible information from the surrounding environment is important in relation with the information provided by the earphone, such audible information from the surrounding environment is lost or difficult to hear with the earphone assembly properly positioned over the ear. Lifting the ear enclosure may be difficult or impossible if the wearer is already engaged in other tasks. Furthermore, the ear might be overloaded with noise from outside, causing interference with or loss of information from the intercom signal, if the ear enclosure were lifted in a noisy environment. Using the nonlinear action of this invention to modify the enclosure wall so as to provide large NR for high level external sounds, and simultaneously to provide small NR for low level external sounds and cause such sounds to combine with signals from the earphone in a common duct leading to the ear, will allow both signals to be heard at an appropriate level. The ear will be protected against the hazardous and/or masking effects of the external sound and will simultaneously receive audible information from both sources.

The nonlinear means for control of noise reduction of an ear muff, as described herein, can be used also to improve the performance of a semi-insert type ear protector that is pressed into and sealed against the opening of the ear canal. The nonlinear element then is designed to control the amount of sound admitted to a small duct passing through the semi-insert protector directly to the ear canal.

The nonlinear means for control of noise reduction as described herein can be used also to passively limit the amount of sound created in the ear canal by a hearing aid which is suddenly exposed to a loud sound or impulse while the electrical gain of the system is set at a comfortable value for amplifying low level signals such as conversation. Electronic circuitry can be, and sometimes is, included within a hearing aid to solve this well-known problem, but that increases the cost, size and power requirement of the hearing aid. For some applications, the use of an electronic limiter may be circumvented advantageously by use of the passive means of the present invention.

The passive, nonlinear means for control of noise reduction, as described herein, also can be used advantageously to limit the amount of sound signal admitted to a microphone, thereby causing the high level noise to encounter more reduction than the lower level audible signals, to prevent its physical damage by excessive excitation and to improve the signal to noise ratio of the electrical output when it is used in a noisy environment.

Numerous other features, objects and advantages of the invention will become apparent from the following spcification when read in connection with the accompanying drawing in which.

Figure 4:
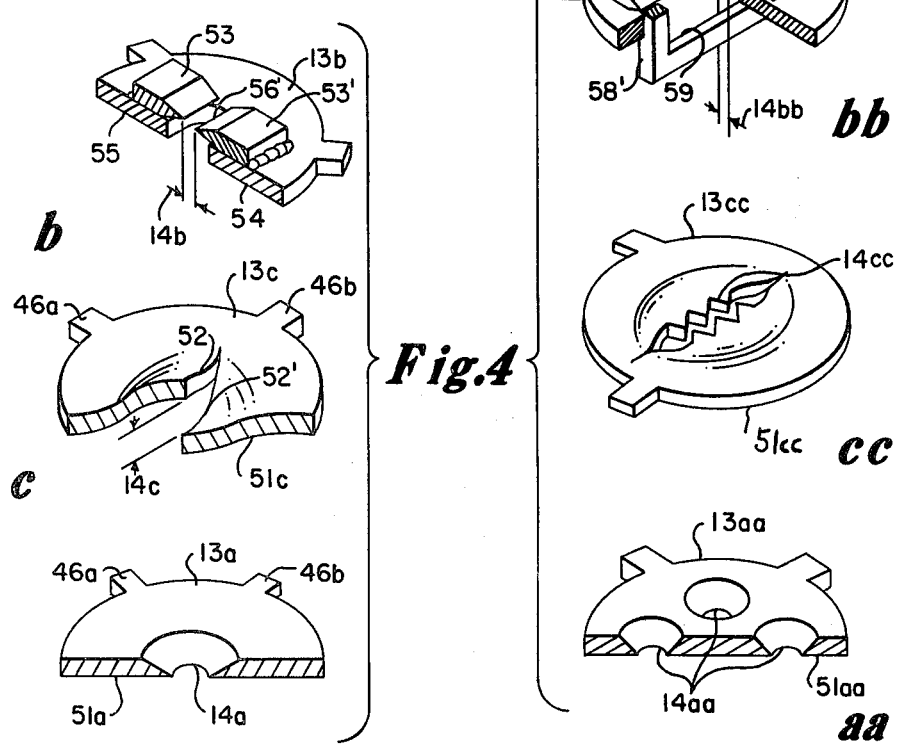
Figure 5:
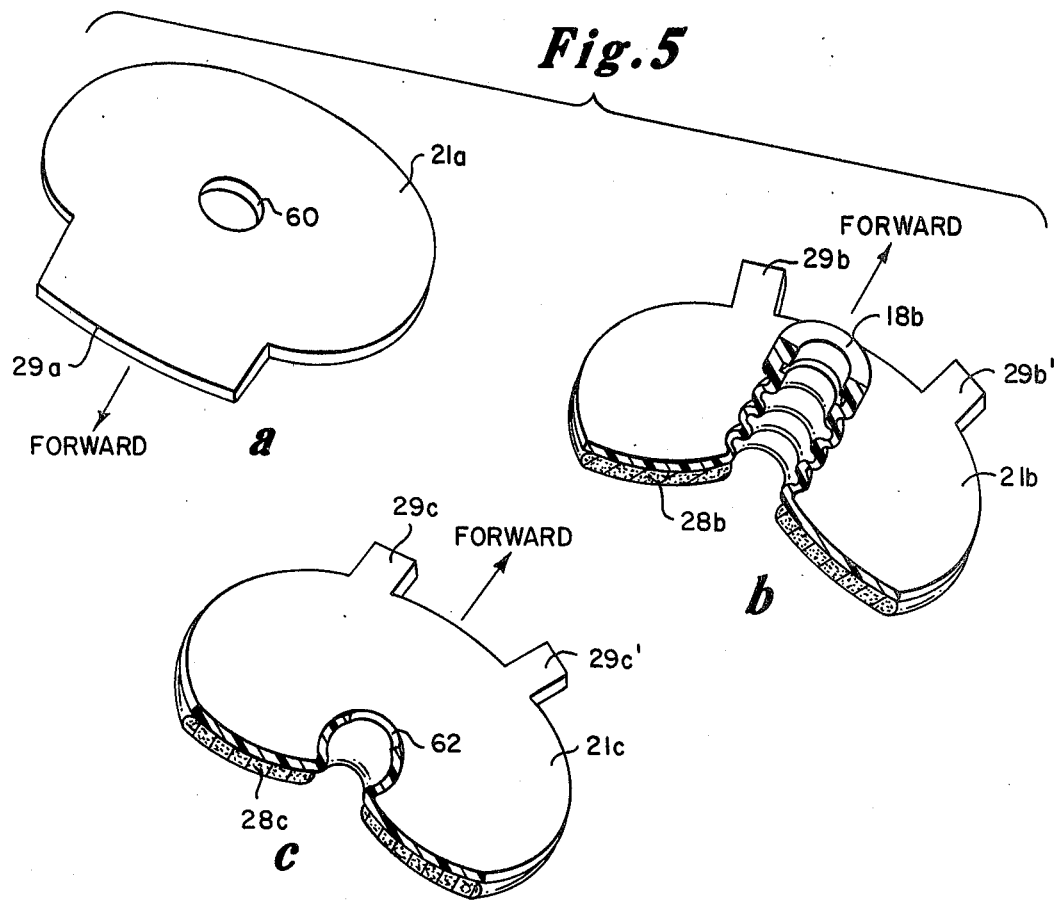
Figure 6:
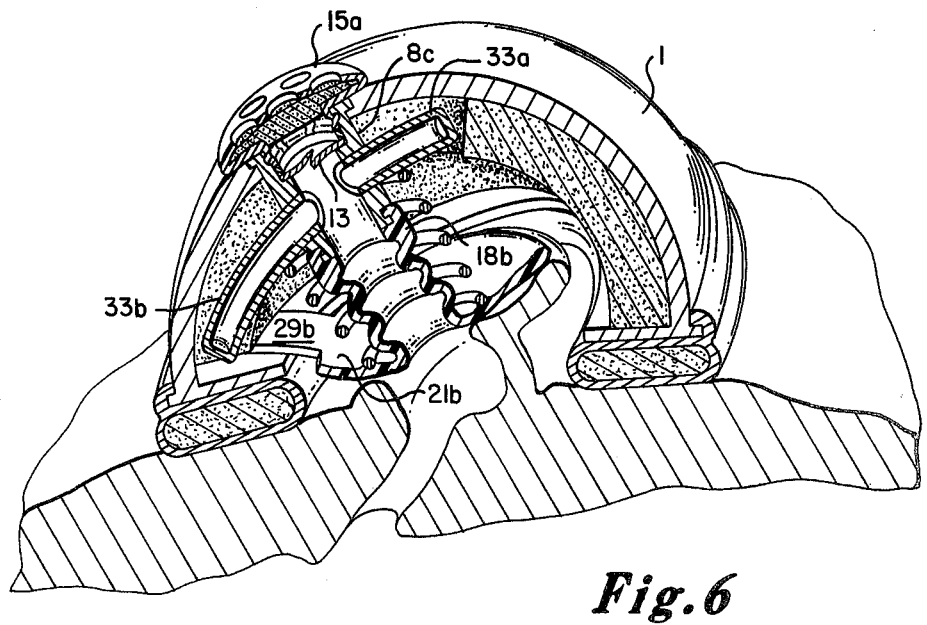
Figure 7:
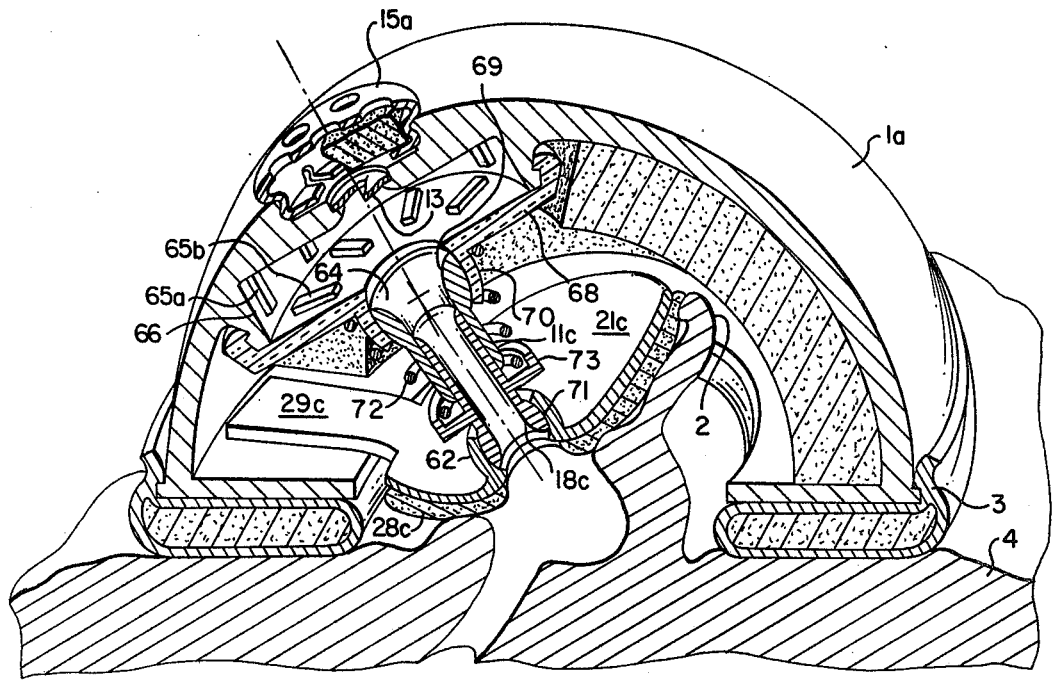
Figure 16:
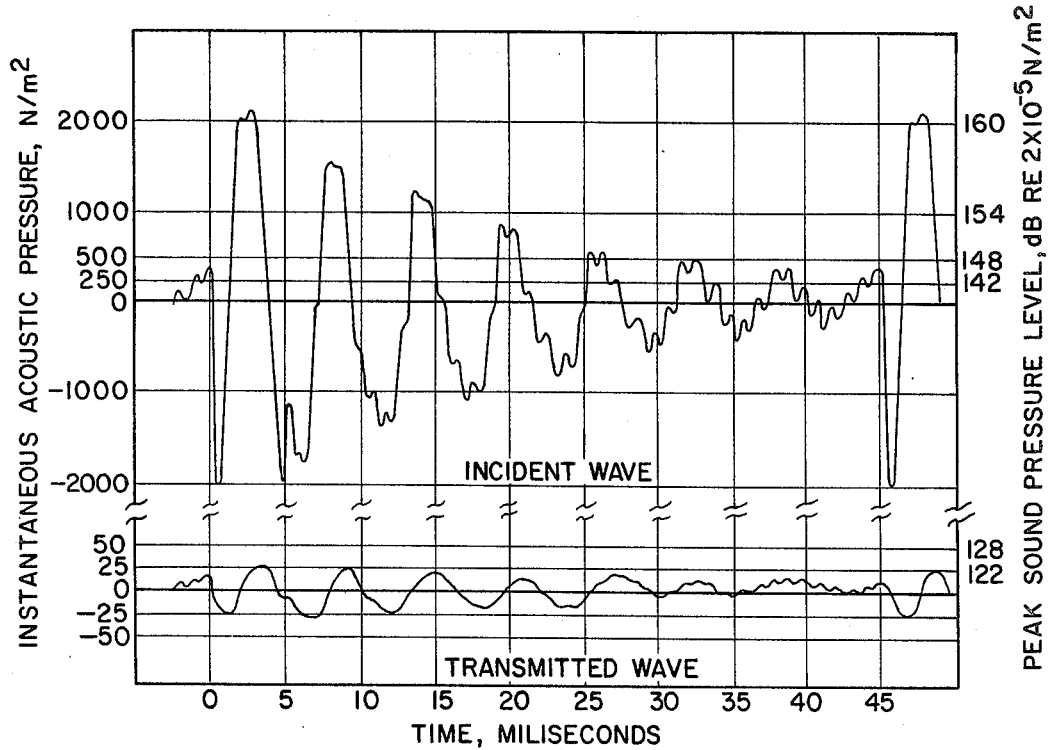
Figure 8:
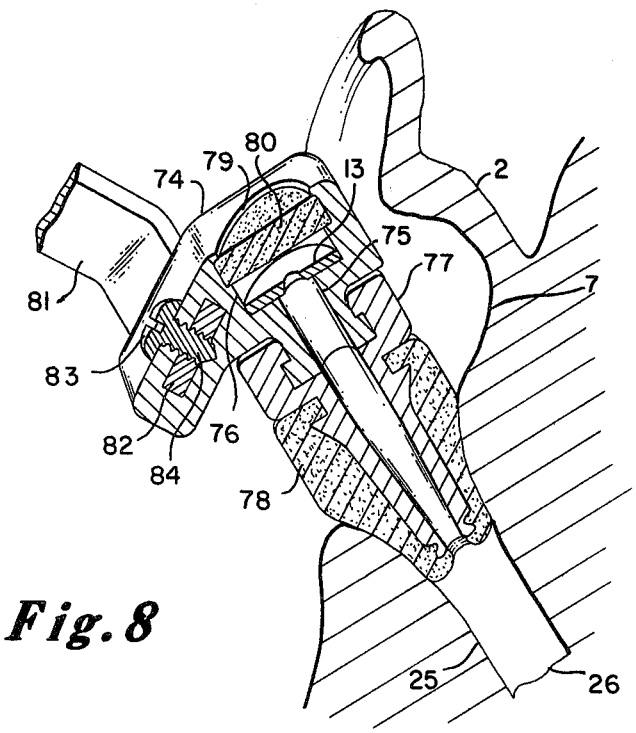
Figure 9:
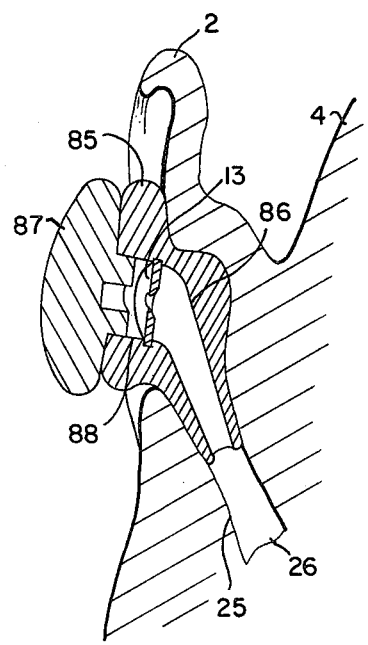
Figure 10:
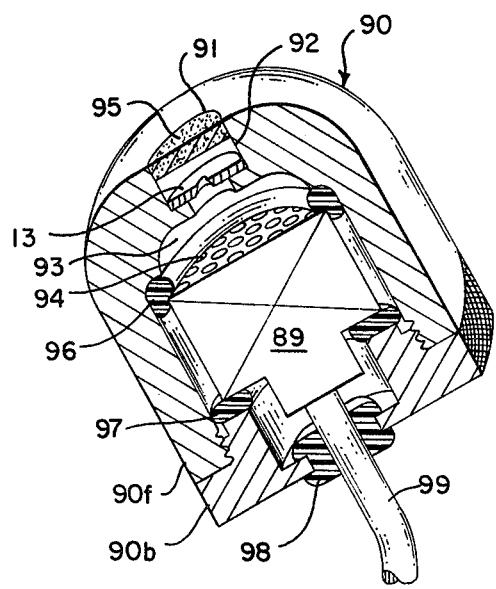
Figure 11:
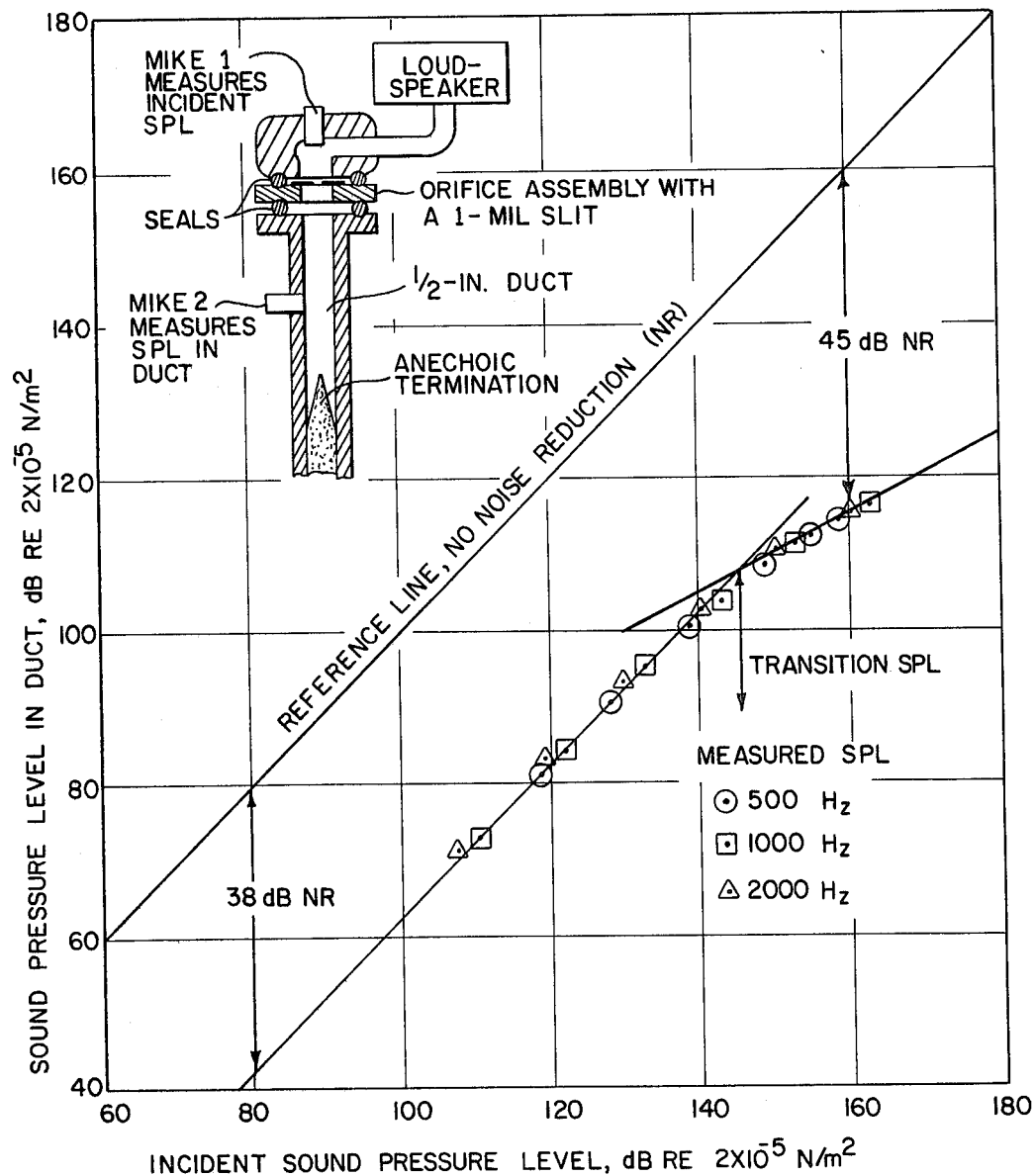
Figure 12:
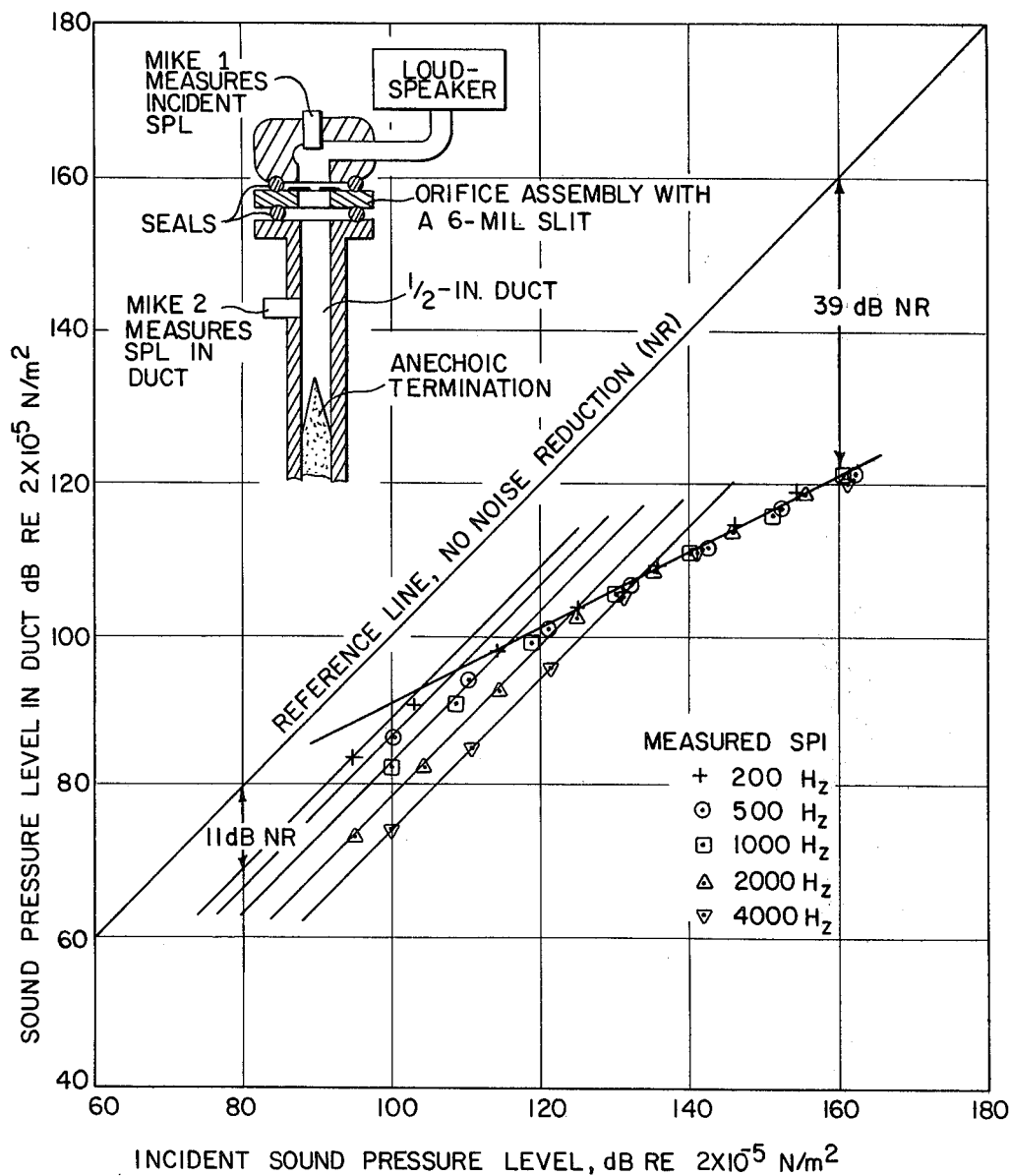
Figure 13:
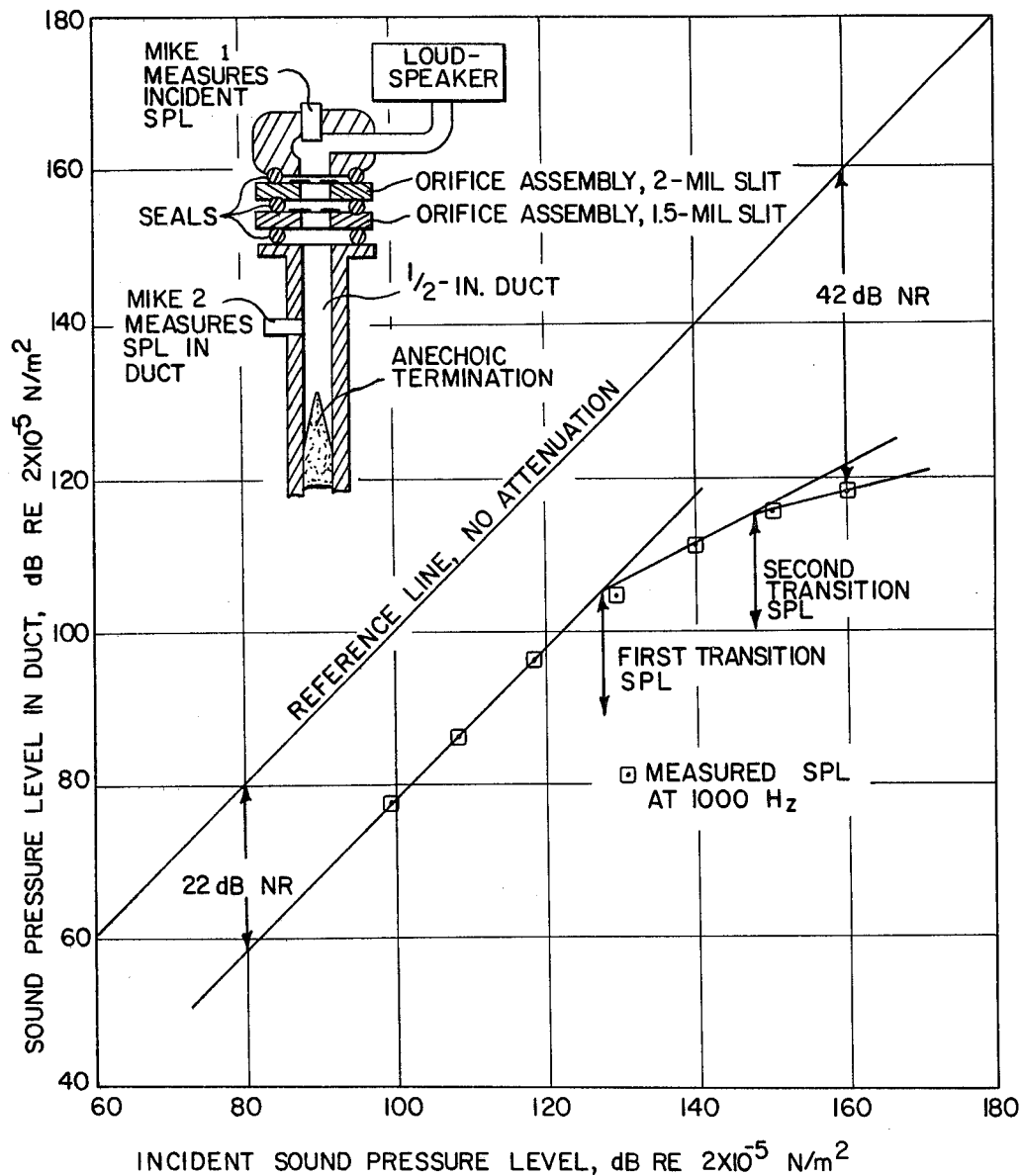
Figure 14:
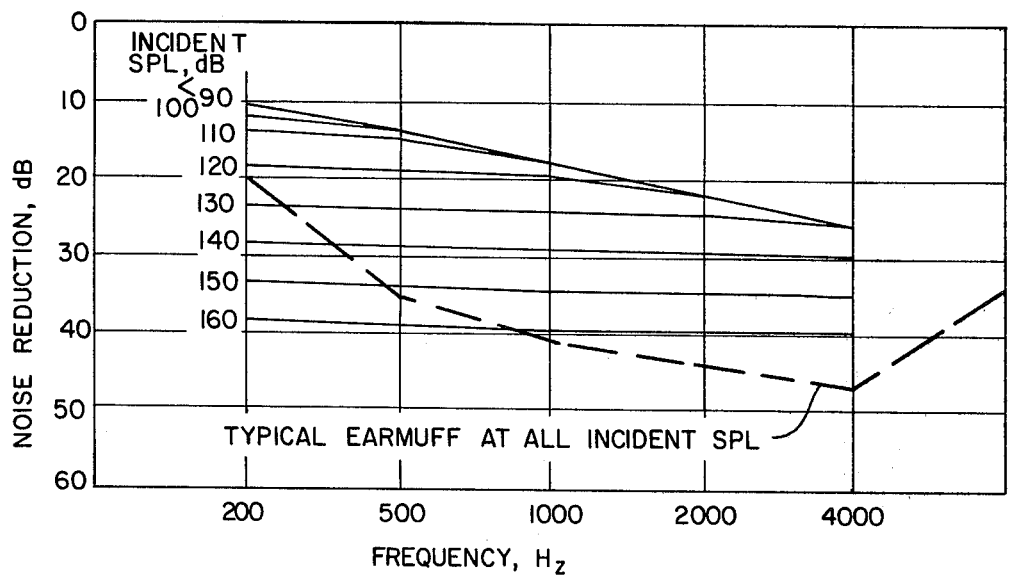
Figure 15:
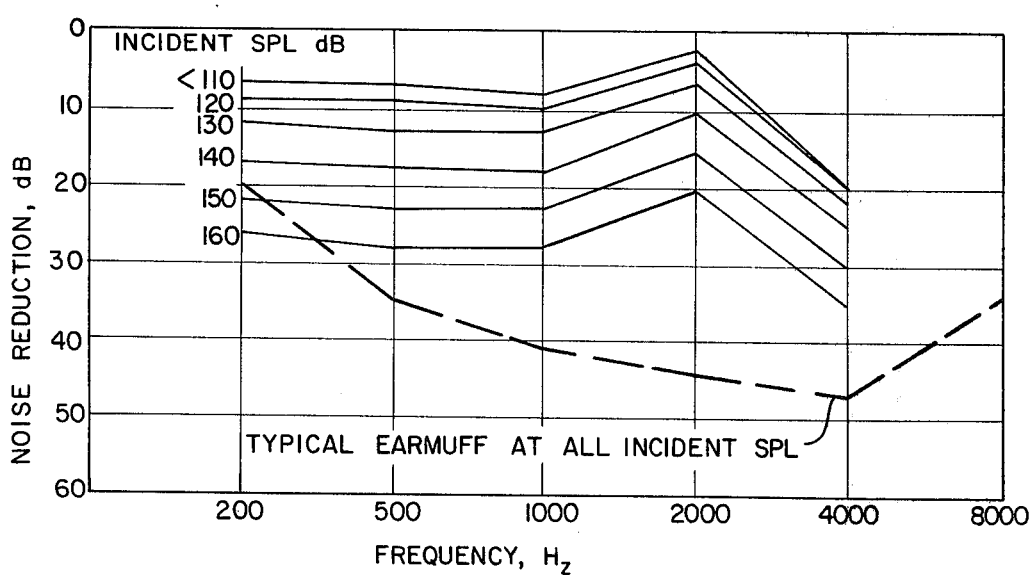

FIGS. 4A-4C, 4AA-4CC are perspective, enlarged views (some in section) of six alternative designs of orifice assemblies;

FIGS. 5A-5C are perspective, enlarged views (some in section) of three alternative designs of the flange member that presses against the ear;

FIG. 6 is a perspective, cross-sectional view of a modified ear muff utilizing another preferred embodiment of the invention;

FIG. 7 is a perspective cross-sectional view of an ear enclosure that includes a receptacle for an earphone and yet another preferred embodiment of the invention;

FIG. 8 is a perspective, cross-sectional view of a semi-insert ear enclosure utilizing another preferred embodiment of the invention;

FIG. 9 is a perspective cross-sectional view of a hearing aid utilizing another preferred embodiment of the invention;

FIG. 10 is a perspective cross-sectional view of a microphone in an enclosure utilizing another preferred embodiment of the invention;

FIG. 11 is a graph presenting experimental data for one embodiment of the invention;

FIG. 12 is a graph presenting experimental data for another embodiment of the invention;

FIG. 13 is a graph presenting experimental data for yet another embodiment of the invention;

FIG. 14 is a graph presenting the experimental sound attenuation data from FIG. 13 in a form that is directly compared with the fixed attenuation of a typical ear muff of conventional design;

FIG. 15 is a graph presenting a similar comparison with other experimental sound attenuation data; and FIG. 16 is a reproduction of a dual-trace oscillograph photograph, demonstrating the real time, instantaneous, effect of the variable attenuation on a sound wave.

Figure 1:
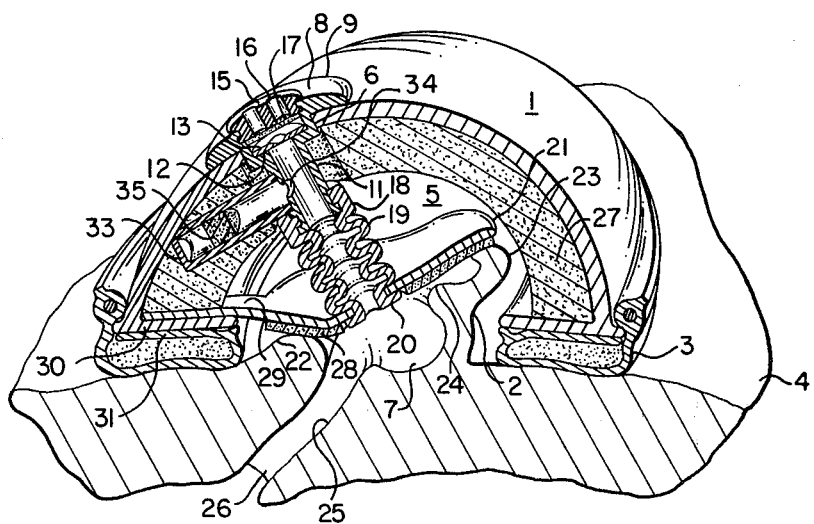
FIG. 1 is a cross section through an ear muff modified with a preferred embodiment of the invention.

Referring now to the drawings and more particularly FIG. 1, wherein there is shown a sectional perspective view of a conventional ear muff assembly, modified with a preferred embodiment of the invention; the assembly is cut horizontally across its center and viewed from below. A typical hard shell 1 covers the external ear 2, and rests on a cushion 3 that presses against the head 4 to provide an acoustic seal, restricting the entrance of sound into the large enclosed cavity 5. Said shell is shown to be modified by a circular hole 6 suitably positioned generally forward of the center of said shell with the center line of said hole directed toward the concha 7 so as to augment high frequency sound signals arriving from the front relative to those arriving from behind the head emulating the unprotected ear.

Figure 2:
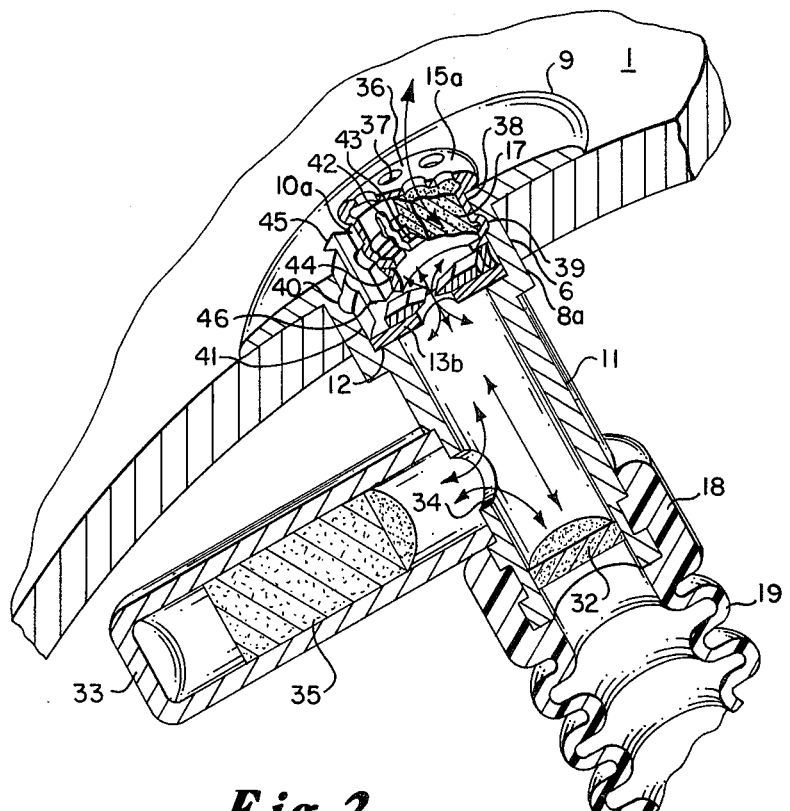
FIG. 2 is a partial section of a portion of FIG. 1 enlarged to show greater detail.

The nonlinear modification that is the subject of this invention is an assembly of functional parts and subassemblies comprising an insert 8, illustrated as insert 8a in FIGS. 1 and 2, that is mechanically held in hole 6. Said insert has an overhanging rim 9 that lies against the outside surface of said shell. A bonding agent may be used to secure the insert in place and seal against any possible air leak or mechanical dislodgment of said insert. Said insert has a central top recess 10a that is open at the bottom to a duct 11 projecting toward the concha 7 leaving a shelf 12 between the opening of the duct 11 and the inner wall of recess 10a that supports and is acoustically sealed to an orifice assembly 13, which in its simplest form, is illustrated in FIG. 1 as a unitary orifice plate 13a comprising a single sharp-edged orifice 14, but said orifice assembly may be any of a number of configurations, such as illustrated in detail in the enlarged views of FIGS. 4A-4C, 4AA-4CC. The external opening of recess 10 is provided with a removable protective grid 15, which fits tightly into recess 10, and has a plurality of holes, such as 16, that are small enough to exclude sizeable objects, but large enough to let sound pass substantially unimpeded. Between said protective grid and said orifice assembly is a replaceable filter mat 17 of porous material, such as fine-pore reticulated polyurethane foam, that has a very low flow resistance and will allow sound to pass substantially undiminished, but will stop dust and similar foreign material that might otherwise collect in said orifice assembly and interfere with its function. Said duct 11 comprises a coacting spring and extensible means, such as 18, that changes length under the influence of a small force exerted by the raised portions of the external ear, the pinna 2, to accommodate whatever differences in distance may exist between said pinna and the shell 1, from one wearer to another, when said ear muff is properly positioned over the ear and sealed by cushion 3 against the head 4 using suitable external force from a headband or other conventional means (not shown). Said extensible means 18 is illustrated in FIG. 1 as a soft, elastomeric, extensible tube having corrugations 19 in its wall that serve as the coacting spring means. The end 20 of the extensible means 18, proximate to said pinna, is integral with a soft, resilient flange 21 that substantially covers the external ear, including the tragus 22, the circumferential helix 23, the anti-helix 24 and (not in view) the anti-tragus and the lobule, all of which, taken as a whole, comprise the pinna 2. Said flange when softly pressed against and generally conforming to the major contours of said pinna aids in confining the sound admitted through the orifice assembly to the region of the duct 11, the concha 7 and the ear canal 25, by restricting the passage of sound toward the large cavity 5 of the ear enclosure beyond the edge of flange 21, thereby increasing the SPL of such sounds at the eardrum 26 and optimizing the performance of the modified ear muff at low sound levels. Said flange also tends to optimize the performance of said modified ear muff at high sound levels by restricting the passage toward the eardrum of the uncontrolled sounds from the large cavity 5 of the ear muff where such sounds are created or are accumulated, in spite of the general use of sound absorbing acoustical foam lining 27, as the shell 1 vibrates due to external acoustic excitation of its natural resonances and as some sound leaks through the seal between the cushion 3 and the head. At high sound levels the nonlinear orifice assembly can produce higher NR than a conventional, unmodified ear muff, as evidenced in FIG. 11; therefore, by helping to exclude noise passage from the large cavity 5, the flange 21 aids in maintaining the higher NR at the eardrum 26. Even greater exclusion of noise and improved comfort can be attained by adding a soft facing 28 of chamois or the like to contact the ear. To keep flange 21 properly positioned with the end 20 of the duct 11 located over the concha 7, said flange is provided with one or more extensions 29 (shown more clearly in the enlargements of FIGS. 5A-5C) projecting forward of the ear and fastened to the inside surface of shell 1 at positions, such as indicated at 30, on the upper surface of the inward extending lip 31 of shell 1. The eardrum 26 does not absorb all sound that strikes it. Experience indicates that a longitudinal resonance of the air column between the orifice assembly and the eardrum 26 can arise and reinforce the SPL at the ear in the frequency region near 2000 Hz. A proper amount of such reinforcement aids in equalizing the spectrum of the NR by counteracting the effect of acoustic mass reactance at the orifice, but as seen in FIG. 12 such reinforcement can be too great. The amount of such reinforcement can be reduced by adding a suitable amount of acoustic absorptive material 32, such as polyurethane acoustical foam, into the duct 11 or extension 18. This would reduce the 2000 Hz resonance, but would also, detrimentally, reduce the SPL at the higher frequencies. A better approach is to use one or more side branch resonators 33, such as a simple closed tube, quarter-wave resonator 33a to reduce the column resonance near 2000 Hz and leave the NR at 4000 Hz (or higher) substantially unaffected. The amount of control provided by such a resonator can be established by procedures, such as choice of the tube length and diameter, the size of the opening 34 into the duct 11 and the amount and location of acoustical absorptive material 35 placed in the resonator 33.

Referring now to FIG. 2 in which a fragment of shell 1 with insert 8 is shown enlarged and in greater detail. Recess 10a, in this instance, holds a more complex orifice assembly 13b (shown in still greater detail in FIG. 4B) and has a protective grid 15a formed of thin metal to give less interference with the passage of sound; it is formed much like the top of a salt shaker having a domed top 36 with perforations 37 and a cylindrical side wall 38 with a circumferential ridge 39 that fits into a corresponding circumferential groove 40 in the cylindrical wall 41 of the recess 10a in insert 8a. Said side wall 38 of protective grid 15a has slots 42 to provide sufficient spring action to permit the ridge 39 to seat securely in groove 40 when protective grid 15a is pressed into recess 10a. The lower edge of said cylindrical side wall 38 of protective grid 15a is bent inward to serve as a ledge 43 to hold, between it and the domed top 36, a replaceable filter, such as filter mat 17. Said ledge may also be used to press a cylindrical, resilient spacer 44 against an orifice assembly, such as 13b, to hold and acoustically seal it against shelf 12 without adhesive sealant or tight frictional retention. Said cylindrical wall 41 of recess 10a has a plurality of longitudinal keyways 45 sized and located to admit correspondingly sized and positioned tabs 46 of an orifice assembly, such as 13b. Said tabs are designed to key each type and size of orifice assembly to a corresponding insert 8, which is then identified by suitable color or other external appearance of its rim 9 so that the performance and application of the modified ear muff can be recognized visually at a glance. Double-pointed arrows, in FIG. 2 indicate the general directions of sound waves within the nonlinear assembly.

Figure 3:
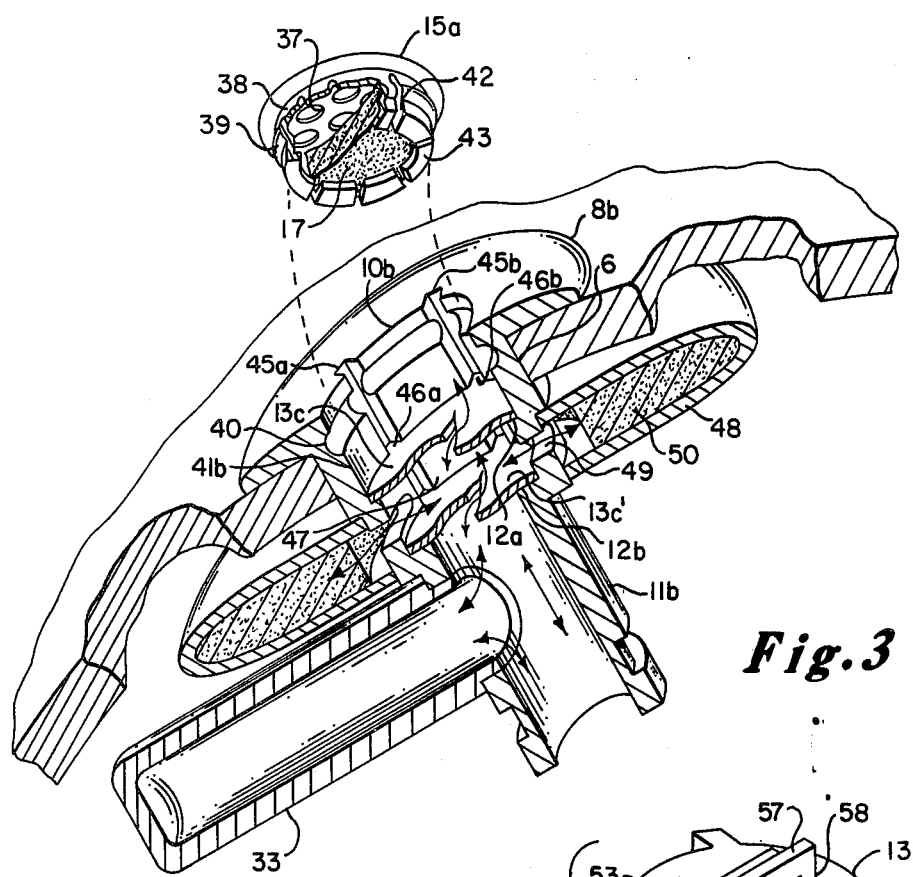
FIG. 3 is a partial section similar to FIG. 2 showing another preferred variation.

FIG. 3 shows a similar fragmentary perspective view of said ear muff shell modified with hole 6 for reception of an insert 8b which accommodates two orifice assemblies in series, such as a first orifice assembly 13c and a second orifice assembly 13c' which preferably are identical (as shown somewhat more enlarged and in greater detail in FIG. 4C), but may be a coacting pair of orifice assemblies that differ in some respects to optimize their cooperative performance or may be slightly different outside diameters to allow accurate spacing between them by firmly pressing them against stepped shelves 12a and 12b in the side wall 41b of recess 10b. Recess 10b is shown with its protective grid 15a lifted so as to better see the details of recess 10b which comprise a circumferential groove 40, two longitudinal keyways 45a and 45b angularly positioned from each other to accept only certain specified orifice assemblies with prescribed performance characteristics, having similarly positioned key tabs 46, such as tabs 46a and 46b of orifice assembly 13c. The use of two orifice assemblies, such as 13c and 13c' in series, provides means for increasing the rate of rise of NR at high intensities. The first orifice assembly provides increasing nonlinear resistance when the incident SPL exceeds a prescribed transition level and causes an increased NR between the external SPL incident upon the ear muff and the internal SPL' develope in the cavity 47 between said first and second orifice assemblies. The second orifice assembly provides increasing nonlinear resistance when the SPL' in cavity 47 exceeds a prescribed second transition level and causes additional NR in the duct 11. The amount of SPL' developed in cavity 47, and therefore the incident SPL required to reach the second transition level, will be determined in part by the volume of cavity 47. For some applications, it may be advantageous to effectively enlarge and modify the acoustical characteristics of cavity 47 by adding a surrounding structure 48a forming a modifying cavity 48, mechanically and acoustically sealed to the exterior surface of duct 11b close to the inner surface of shell 1 and communicating with the cavity 47 through one or a plurality of openings 49 therebetween. The acoustical function of the modifying cavity may be tailored by choice of its dimensions, the dimensions and number of openings 49 and the amount, quality and location of acoustical absorbing material 50 included inside the combined space of cavities 47 and 48 and openings 49.

Referring to FIGS. 4A-4C, 4AA-4CC there are shown six alternative designs of orifice assemblies typical of designs which have been utilized, but do not constitute limitations upon the practical embodiments that can be produced economically to perform the nonlinear acoustical functions falling within the scope and principles of the novel design disclosed in the present invention. Orifice assembly 13a is basically a simple, round, thin plate with a single, round sharp-edged orifice 14a at its center, similar to orifices that have been used in earplugs for over 20 years, as is well-known to those experienced in the art. Orifice assembly 13aa is a similar design using a plurality of round, sharp-edged orifices 14aa for the purpose of reducing the total effective acoustical mass reactance of the assembly. Orifice 13c is again basically a thin, round plate with an orifice 14c in the form of a simple punched slit having the acute edges 52 and 52' characteristic of such punched slit, adjacent to each other, forming an elongated acute-edged opening 14c having generally less acoustical mass reactance at high frequencies than a single, round, sharp-edged orifice of the same open area and less total viscous resistance at low sound levels than a plurality of round orifices of similar total open area and total acoustical mass reactance effective at high frequencies.

Orifice assembly 13cc is a similar thin round plate 51cc with a sawtooth-shaped punched slit 14cc intended to increase the instability of the airflow as needed to initiate the onset of turbulence at a lower flow speed, thereby to advantageously lower the transition SPL. Orifice assembly 13b represents a completely new orifice design using razor blades 53 and 53' fastened and sealed to a washer-shaped base plate 54 and positioned over the center opening 55 in said plate 54 so as to form a slit 14b with the sharpest possible edges 56 and 56' to minimize the air flow speed necessary to produce turbulence with a sharp-edged orifice of a specified width by itself, operating between specified acoustic environments. With orifice assemblies of the type 13b, values of transition SPL as low as 104 dB re $2 \times 10^{-5}$ N/M have been attained at 200 Hz.

To initiate turbulence in the air stream at lower air speeds it is necessary to trigger the turbulence by interfering with the streamline airflow in the jet produced by the orifice. One arrangement to accomplish this process is illustrated by the orifice assembly 13bb utilizing two razor blades 53 and 53' mounted as in orifice assembly 13b, to form an orifice, but utilizing also a frame 57 comprising end members 58 and 58' supporting and positioning interfering members 59 and 59', preferably with knife edges, therebetween located a distance of typically one to five times the width of orifice 14bb away from the plane of said orifice, and lying along the length of said orifice so as to intercept at least a portion of the jet of air ejected alternately in one direction then the other created by the alternating pressure difference across the orifice due to the incident sound wave. This same principle of interfering with a jet could be applied equally well to a round orifice or any orifice or plurality of orifices of arbitrary shape or configuration.

Referring to FIGS. 5A-5C, there are shown three alternative designs of resilient flange 21. FIG. 5A shows a simple sheet 21a, such as of neoprene rubber, cut to a shape that covers the pinna and has a central hole 60 fitting securely around end 20 of duct extension 18 and having an extension 29 projecting forward of the ear to enable fastening to shell 1 as explained above. FIG. 5B comprises a similar resilient flange 21b that is molded in one piece with resilient duct extension 18a and two forward projecting attachment extensions 29b and 29b' as is apparent from the cross section illustrated and viewed looking forward. Soft facing 28b, such as chamois or resilient foam, with high resistance to airflow is shown attached to the lower face of flange 21b. FIG. 5C shows a partial section of a third preferred embodiment of said resilient flange 21C comprising a molded form having a partial spherical socket 62 at its center designed to fit and swivel on the end 20c of duct extension 18c as illustrated in FIG. 7. A soft facing 28c is shown.

FIG. 6 shows a view similar to FIG. 1 illustrating another preferred embodiment in which said insert 8 is shown as insert 8c having two side branch resonators 33a and 33b for control of an additional resonance. Said insert is shown recessed flush with the outer surface of shell 1, which itself may be coded visually to indicate the type of orifice assembly 13 it accommodates and the type of environment for which it is applicable. The spring means of the corrugated duct extension 18b that is molded in one piece with resilient flange 21b is augmented by a coacting helical steel spring 63 to increase the reliability of restricting the passage of sound between the resilient flange 21b and the pinna 2.

FIG. 7 presents another preferred embodiment of the invention adapted for use with an earphone. In this instance the shell 1a is shown molded with an internal pillbox 64, shaped to fit an earphone (not shown) that is held away from the pillbox surfaces by ribs 65, such as ribs 65a on the cylindrical wall 66 extending onto the flat surface 67 of the pillbox and ribs 65b on the inside of the cover 68, to allow space for sound to travel around the outside of said earphone from orifice assembly 13 to duct 11c which is formed with a partial sphere 69 at the upper end that snaps into and swivels freely in the ball socket 70 in the center of cap 68 as necessary to align said duct with its extension 18c that fits with smooth sliding action within duct 11c to accommodate variations in length of said duct when the ball end 71 of duct extension 18c is snapped into spherical socket 62 of resilient flange member 21c and pressed toward the pinna 2 by helical spring member 72 which presses against cap member 68 and against duct extension member 18C through spring shelf 73.

Referring to FIG. 8, there is shown an enlarged cross-sectional, perspective view of a semi-insert ear protector of novel design utilizing another preferred embodiment of the invention. Said semi-insert ear protector comprises a shell 74 having a through-duct 75 designed to be axially directed toward the ear canal 25 of the wearer when properly worn. Said duct holds an orifice assembly 13 in secure, acoustically sealed relation with the wall 76 of an enlarged portion of duct 75 to provide a prescribed nonlinear NR in the region between said orifice assembly and the eardrum 26, confined by the duct extension 77 that projects toward and acoustically seals against the opening of ear canal 25 with the aid of soft, deformable, slowly resilient cushion member 78. The external end 79 of said duct is protected against the entrance of foreign material by a protective member 80 that may preferably comprise a rigid porous disc of sintered metal fiber, providing negligible attenuation in the passage of sound into said duct, mechanically held in place, for example, by a tight frictional edge contact with duct wall 76. Said semi-insert ear protector comprises an assembly of said shell 74 and a means of support such as headband 81, fastened by suitable means such as slot 82 in shell 74 that accepts the end of said headband and screw 83 that penetrates said shell material and engages tightly with threaded hole 84 in the end of said headband, to hold said assembly securely together.

FIG. 9 shows a cross-sectional perspective view of a hearing aid comprising a molded shell 85 shaped to project into an ear canal 25 and provided with a central duct 86 leading to the ear canal from a conventional hearing aid earphone 87 fitted and acoustically sealed into the enlarged end 88 of said central duct, and comprising an orifice assembly 13 fastened in an acoustically sealed relation with said duct to produce nonlinear reduction of the sound created by said earphone as it passes through said orifice assembly into said central duct leading to said ear canal.

FIG. 10 shows a perspective, cross-sectional view of a microphone 89 of conventional design, modified with an enclosing assembly utilizing the nonlinear means of the present invention. Said enclosing assembly comprises a shell 90 defining an opening 91 and excluding the passage of any airborne external sound to any surface of said microphone except through said opening, an orifice assembly 13 held in an acoustically sealed relation with the wall 92 of said opening to provide a nonlinear attenuation of the incident sound as it enters the cavity 93 above the face 94 of said microphone through said orifice assembly, a porous cover 95 for said opening, such as might be made of sintered metal fiber or sintered metal or ceramic particles or comprised of a protective grid and filter mat as before described to prevent the entrance of foreign matter that might interfere with the performance of said orifice assembly, and suitable vibration isolating, resilient, elastomeric gaskets such as 96, 97 and 98 to vibrationally isolate said microphone from said shell and provide acoustical seals between connecting members such as the front shell member 90f and the back shell member 90b and wire lead 99.

FIG. 11 is a graphic presentation of experimental data. It shows the nonlinear sound reduction (NR) produced by an orifice assembly such as 13b of FIG. 4B comprising a slit 1-mil (0.001 inch) wide, approximately ½ inch long between the parallel, sharp edges of two razor blades cemented to a steel washer. The test arrangement, illustrated schematically in FIG. 11, comprised a loud speaker sound source ducted to the orifice assembly, a calibrated first microphone measuring the SPL incident upon the orifice assembly, a ½ inch diameter, anechoically terminated duct following the orifice assembly and a calibrated second microphone sealed into the wall of the duct to measure the SPL of the progressive sound wave admitted to the duct through the orifice assembly.

At incident sound pressure levels (SPL) below a transition level of approximately 146 dB re $2 \times 10^{-5}$ N/m$^2$, the NR is independent of the incident sound pressure level. Above 146 dB the NR increases at a rate approaching 5 dB for an increase of 10 dB in the incident sound pressure level. The NR and the transition level observed for this arrangement are independent of the frequency over the frequency range tested. Below the transition level, the NR is controlled by the resistive component of acoustic impedance that is due to viscous flow; it is substantially independent of frequency and also independent of sound amplitude. Above the transition level, the NR is controlled primarily by the resistive component of acoustic impedance that is due to turbulence; again, this resistive component is substantially independent of frequency, but it increases directly with the incident sound pressure and accounts for the steady increase in NR with increase in the incident SPL.

FIG. 12 shows experimental data for a similar test arrangement using an orifice assembly comprising a slit 6-mils wide and 1/16 inch long between parallel razor blade edges. For this wider slit, having roughly the same open area, the resistive component of acoustic impedance due to viscous flow through the orifice at the low sound levels is greatly reduced and is less than the mass reactive component of impedance due to the inertia of the air as it is forced to reverse direction of motion, back and forth, through the orifice. The mass reactive component of acoustic impedance increases directly with the frequency and so accounts for the greater NR at the higher frequencies observed in FIG. 12 for low values of incident SPL. However, like the resistive component, the reactive component is independent of the incident SPL and so for each frequency tested, the NR remains constant at low SPL until the incident SPL rises to a transition SPL which is progressively higher at each higher frequency.

Above the transition SPL the acoustic impedance of the orifice assembly is dominated by the resistive component of impedance due to turbulence; that component is again substantially the same for all frequencies tested from 200 to 4,000 Hz. That resistive component increases as the incident SPL increases and causes the NR to increase 5 dB for each increase of 10 dB in SPL. In this region, above the transition SPL, the resistive component is substantially the same for all frequencies over the range tested and the NR values for all frequencies lie on a single straight line.

FIG. 13 shows experimental data for a similar test arrangement using two orifice assemblies in series. Measurements at the single frequency of 1000 Hz show an NR that is constant below the transition SPL near 127 dB then shows an NR increasing at the rate of 5 dB for 10 dB increase in incident SPL until a second transition SPL is reached near 147 dB whereupon the NR continues to increase, but at a rate of 7½ dB for each 10 dB increase in incident SPL.

FIG. 14 presents data from FIG. 12 in a form that allows a direct comparison between the unchanging NR characteristic of a conventional ear muff and the nonlinear, amplitude-sensitive NR produced by the present invention operating into an anechoically terminated duct. It is seen that the NR produced by the amplitude sensitive orifice assembly of this invention, allows sounds of low incident levels to be heard with greatly reduced NR, but sounds of sufficiently high levels encounter an NR approaching that of a conventional unmodified ear muff.

FIG. 15 shows a similar set of data for a narrower orifice operating into a simulated ear canal where the second microphone was located at the simulated eardrum position. The results indicate a reinforcement of SPL at the eardurm location due to an acoustic resonance.

To illustrate the operation of the nonlinear orifice in real time, FIG. 16 presents a copy of an oscillograph trace of the incident and the transmitted sound wave as photographed using the chopped mode on a single beam, dual trace oscilloscope so that both sound signals could be observed simultaneously. The electrical gain of the amplifier in the channel for the transmitted sound wave was set 20 dB higher (a factor of 10 in amplitude) than that for the amplifier in the channel for the incident wave to partially account for the NR of the orifice element in the acoustic system and thus to allow the wave shapes of both signals to be compared visually on the same screen. The loudspeaker was pulsed with an exponentially decaying 200 Hz signal approximately once every 45 milliseconds. This signal can be viewed to represent a high SPL impact from a forging hammer or the like. Mixed with the electrical signal input to the loudspeaker is a low level 1000 Hz continuous tone of constant amplitude. This signal can be viewed to represent a low level voice or warning signal. The mixture of these two signals is clearly visible in the upper trace in FIG. 16. The lower trace shows the transmitted signal. The observation to be made is that the large amplitude 200 Hz signal is reduced much more than the low amplitude 1000 Hz signal. Furthermore, although the low level, 1000 Hz signal cannot be observed when the 200 Hz impulse signal is very loud, it can be clearly observed in the intervals when the 200 Hz signal has a low value. The same holds for the ability of the ear to hear.

Note also, that without a hearing protector, although the 1000 Hz signal SPL was adjusted to a level of approximately 128 dB rms, it probably could not be heard immediately after the 200 Hz impulse such as the one illustrated, which reached a peak level of 160 dB, because the impulse would cause a ringing in the ears that would mask the weaker signal for an extended period of time.

With conventional ear muff hearing protectors the 200 Hz signal would be reduced approximately 20 dB as seen in FIG. 14 and might still cause some ringing of the ears at its new level of 140 dB (maximum impulse peak level allowed by the current, 1982, OSHA limit). At the same time the 1000 Hz tone would be reduced by 40 dB and would have a level of only 88 dB at the ear. The difference in level between the 200 Hz impulse peak and the 1000 Hz signal would be increased with the conventional ear muff and the 1000 Hz signal made more difficult to hear, as indicated in the table below.

|  | Incident SPL | With Ear Muff | | | |
|---|---|---|---|---|---|
|  |  | Conventional | | Nonlinear | |
|  |  | NR | SPL | NR | SPL |
| 200 Hz | 157 | 20 | 137 | 38/20* | 137 |
| 1000 Hz | 128 | 40 | 88 | 24 | 104 |
|  | 29 |  | 49 |  | 33 |

*The NR of an ear muff modified with a nonlinear element would be limited at high sound levels not to exceed the maximum NR of the unmodified ear muff shell and cushion, so, although the nonlinear element can provide 38 dB NR at 200 Hz, the modified ear muff of the design illustrated in FIG. 11 would be limited to 20 dB NR at 200 Hz. Even so, the 1000 Hz signal is much more easily heard with the modified than with the unmodified ear muff.

The ear muff performance characteristics described by the data presented in FIGS. 11–16 are not optimized for any specified service conditions; they illustrate the nature of the nonlinear change in the noise reduction that can be effected in a passive system.

There has been described novel apparatus and techniques for passively attenuating loud noise while transmitting sound at lower levels bearing information to the ear. It is evident that those skilled in the art may now make numerous uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. In a sound reducing or attenuating enclosure comprising a rigid, massive, shell, the improvement comprising passive means for continuously altering the effective sound reduction or attenuation of said enclosure as a function of the instantaneous amplitude of the pressure of the sound incident upon said enclosure over at least a portion of the audio frequency range between 20 and 20,000 Hz, said passive means comprises an orifice assembly defining at least one sharp-edged orifice and arranged in acoustically sealed relation with a hole in said shell of said enclosure, thereby preventing the entrance of any significant amount of sound into said enclosure through said hole except for such supplemental sound as may be permitted through the small open area provided by said at least one sharp-edged orifice in said orifice assembly and admits air flow into and out of said enclosure in a nonlinear, amplitude sensitive relation for allowing supplemental sound to enter said enclosure and to combine with sound entering inside said enclosure by other paths and constraining the pressure amplitude of said supplemental sound to be in a substantially direct proportion to said incident sound pressure amplitude when said incident sound pressure amplitude is below a prescribed transition value within the range corresponding to a sound pressure level of 90 to 140 dB re $2 \times 10^{-5}$ N/m$^2$ and constraining the pressure amplitude of said supplemental sound to approach a relationship substantially proportional to the square root of said incident sound pressure amplitude as said incident sound pressure amplitude rises above said prescribed transition value.

2. Apparatus for passively altering the sound reduction of an enclosure in accordance with claim 1 wherein the total area of opening in said passive means lies in the range from 0.0001 to 0.005 square inch.

3. Apparatus for passively altering the sound reduction of an enclosure in accordance with claim 1 wherein said sound reducing enclosure is defined by a circumaural ear muff shell pressed against a cushion providing an acoustic seal against the surface of the head around the ear and wherein said passive means comprises a duct, one end of said duct being in sealed connection with said ear muff shell around said opening in said shell and the other end of said duct extending so as to be in close proximity to the ear canal when said ear muff is properly positioned against the head.

4. Apparatus for passively altering the sound reduction of an ear muff in accordance with claim 3 wherein said duct is extensible and further comprising resilient spring means coacting with said duct for directing the extended end of said duct toward the position of the opening of the ear canal and adjusting said duct length to accommodate normal variations in ear size while exerting a small force against the external ear when said ear muff is properly positioned over the ear and pressed in place against the head.

5. Apparatus for passively altering the sound reduction of an ear muff in accordance with claim 4 and further comprising side branch acoustic circuit means communicating with said duct for counteracting at least the first longitudinal resonance mode of said duct so as to enhance the spectral uniformity of the noise attenuation that is effected at the ear canal over the frequency range from 100 to 4000 Hz when said instantaneous amplitude of the pressure of said sound wave incident upon said ear muff is below said prescribed transition value.

6. Apparatus for passively altering the sound reduction of an ear muff in accordance with claim 4 wherein the end of said duct proximate to the opening of said ear canal has a resilient flange, shaped and oriented to lie against the pinna to aid in confining the sound that is transmitted from the orifice assembly toward the ear and restricting the passage of sound between the region of the ear canal and the larger cavity within the ear muff shell outside said duct.

7. Apparatus for passively altering the sound reduction of an ear muff in accordance with claim 3 wherein said passive means constrains said supplemental sound to be transmitted to the ear canal with substantially no uncontrolled phase alteration such that any phase change developed between the sound wave incident upon the ear muff and the sound arriving at the ear will be substantially the same for both ears when both are protected by said apparatus, thereby permitting coherent binaural reception of the sound that enables such directional location of identifiable sources as is normally possible in a free acoustic field of moderate sound levels without ear muffs.

8. Apparatus for passively altering the sound reduction of an ear muff in accordance with claim 3 wherein said passive means comprises an insert assembly for coupling to a single hole through said shell.

9. Apparatus in accordance with claim 8 wherein said insert has a recess with a keyed shape for receiving an orifice assembly defining at least one sharp edged orifice and having a keyed shape corresponding to the shape of said recess to assure that only an orifice assembly constructed for a particular application can be assembled with said insert and wherein said insert has a sensible coding means for providing highly obvious and permanent identification of the appropriate application of the ear muff so modified.

10. Apparatus in accordance with claim 1 wherein said passive means comprises a protective rigid structure and a fine-pore filter material coacting to exclude sizeable objects, dust and other matter that might impair the performance of said orifice assembly and simultaneously offering negligible attenuation of incident sound waves.

11. Apparatus in accordance with claim 6 wherein said resilient flange has a soft facing such as chamois or a deformable foam with high flow resistance and slow resilience to yield and deform around the prominent surfaces of the external ear.

12. Apparatus for passively altering the sound reduction of an enclosure in accordance with claim 3 and further comprising an earphone,
said duct surrounding said earphone and provides space for said supplemental sound admitted by said passive means to pass by said earphone and add to a sound created electrically by said earphone as both sounds are conducted through the extension of the duct to the ear canal.

13. Apparatus for passively altering the sound reduction of an enclosure in accordance with claim 1 wherein said sound reducing enclosure comprises the hard shell of a semi-insert ear protector pressed against a cushion member at the opening of the ear canal of the wearer and said passive means comprises a duct communicating with the atmophsere at its open end, passing through said semi-insert ear protector and said cushion, and opening into the ear canal of the wearer at its other end, and comprising an orifice assembly closing said duct near said open end except for the small open area of at least one sharp-edged orifice defined by said orifice assembly.

14. Apparatus for passively altering the sound reduction of an enclosure in accordance with claim 13 and further comprising an earphone,
said duct surrounding said earphone and provides space for said supplemental sound admitted by said orifice assembly to join with a sound created electrically by said earphone as both sounds are conducted through said duct and into said ear canal.

15. Apparatus for altering the sound reduction of an enclosure in accordance with claim 1 wherein said noise reducing enclosure comprises the hard shell that is associated with a hearing aid and that is constructed to project into and seal against the opening of the ear canal of the wearer and that has an internal cavity in the form of a duct communicating at one end with the opening of a hearing aid earphone and opening at the other end into said ear canal, and wherein said passive means comprises an orifice assembly closing said duct at a position close to said opening of said hearing aid earphone, except for the small area of at least one sharp edged orifice defined by said orifice assembly acting passively to provide a variable amount of sound reduction for the sound produced by said hearing aid earphone incident upon said orifice assembly and entering the enclosed space comprising the duct within the hard shell of said hearing aid and the ear canal between the ear drum and said orifice assembly.

16. Apparatus for passively altering the sound reduction of an enclosure in accordance with claim 1 and further comprising a microphone, said sound reducing enclosure comprising a rigid massive shell surrounding and shielding said microphone from all incident airborne sound.

17. Apparatus for passively altering the sound attenuation of an enclosure in accordance with claim 1 wherein said orifice assembly comprises a structure defining at least one sharp-edged slit.

18. Apparatus for passively altering the sound attenuation of an enclosure in accordance with claim 17 wherein said slit has an open width lying between 0.001 and 0.025 inch.

19. An apparatus for passively altering the sound reduction of an enclosure in accordance with claim 1 wherein said orifice assembly comprises a solid spoiler that intercepts at least a potion of the air jet formed on each side of said orifice in response to high values of said instantaneous sound pressure amplitude of said incident sound wave.

20. An apparatus for passively altering the noise reduction of an enclosure in accordance with claim 1 wherein said passive means comprises at least two said orifice assemblies arranged in series forming an intermediate cavity between each two orifice assemblies.

21. An apparatus for passively altering the noise reduction of an enclosure in accordance with claim 20 wherein said intermediate cavity is augmented by an additional cavity, acoustically communicating therewith.

* * * * *